United States Patent
Booker et al.

(10) Patent No.: US 6,998,372 B2
(45) Date of Patent: Feb. 14, 2006

(54) MOISTURIZING DETERGENT COMPOSITIONS

(75) Inventors: Gregory Booker, Philadelphia, PA (US); Joseph Librizzi, Neshanic, NJ (US); Delores Santora, Hillsborough, NJ (US)

(73) Assignee: J&J Consumer Companies, Inc., Skillman, NJ (US)

( * ) Notice: Subject to any disclaimer, the term of this patent is extended or adjusted under 35 U.S.C. 154(b) by 489 days.

(21) Appl. No.: 09/931,703

(22) Filed: Aug. 16, 2001

(65) Prior Publication Data

US 2003/0114323 A1 Jun. 19, 2003

(51) Int. Cl.
C11D 1/14 (2006.01)
C11D 1/62 (2006.01)
C11D 1/72 (2006.01)
C11D 3/20 (2006.01)

(52) U.S. Cl. .................. 510/124; 510/126; 510/130; 510/137; 510/138; 510/155; 510/158; 510/159; 510/476; 510/470; 510/499; 510/501; 510/504

(58) Field of Classification Search .......... 510/124, 510/126, 130, 137, 138, 155, 158, 159, 476, 510/470, 479, 501, 504
See application file for complete search history.

(56) References Cited

U.S. PATENT DOCUMENTS

| | | | |
|---|---|---|---|
| 4,002,758 A | 1/1977 | Bigou | |
| 4,381,259 A | 4/1983 | Homma et al. | |
| 4,488,564 A | 12/1984 | Grollier et al. | |
| 4,595,586 A | 6/1986 | Flom | |
| 4,650,661 A | 3/1987 | Szelke et al. | |
| 4,666,707 A | 5/1987 | Eguchi et al. | |
| 4,794,106 A | 12/1988 | Takashima et al. | |
| 4,812,253 A | 3/1989 | Small et al. | |
| 4,929,439 A | 5/1990 | Cotteret et al. | |
| 4,963,535 A | 10/1990 | Sebag et al. | |
| 4,992,476 A | 2/1991 | Geria | |
| 5,085,857 A | 2/1992 | Reid et al. | |
| 5,138,043 A | 8/1992 | Polovsky et al. | |
| 5,324,507 A | 6/1994 | Dubief et al. | |
| 5,344,650 A | 9/1994 | Otsuka et al. | |
| 5,384,334 A | 1/1995 | Polovsky et al. | |
| 5,405,878 A | 4/1995 | Ellis et al. | |
| 5,422,031 A | 6/1995 | Nomura et al. | |
| 5,529,721 A | 6/1996 | Salka et al. | |
| 5,536,332 A | 7/1996 | Chun | |
| 5,567,359 A | 10/1996 | Cassidy et al. | |
| 5,612,307 A | 3/1997 | Chambers et al. | |
| 5,635,461 A | 6/1997 | Onitsuka et al. | |
| 5,756,078 A | 5/1998 | Oppenlander et al. | |
| 5,766,628 A | 6/1998 | Nürnberg et al. | |
| 5,783,535 A | 7/1998 | Isobe et al. | |
| 5,804,540 A | 9/1998 | Tsaur et al. | |
| 5,837,661 A | 11/1998 | Evans et al. | |
| 5,871,758 A | 2/1999 | Nagy et al. | |
| 5,882,666 A | 3/1999 | Averill et al. | |
| 5,916,575 A | 6/1999 | McAtee et al. | |
| 5,942,479 A | 8/1999 | Frankenbach et al. | |
| 6,045,145 A | 4/2000 | Lan | |
| 6,090,773 A | 7/2000 | Allan et al. | |
| 6,153,208 A * | 11/2000 | McAtee et al. | 424/402 |
| 6,156,297 A | 12/2000 | Maurin et al. | |
| 6,180,576 B1 | 1/2001 | Melby et al. | |
| 6,194,364 B1 | 2/2001 | Glenn, Jr. | |
| 6,224,886 B1 | 5/2001 | Charlton et al. | |
| 6,277,798 B1 * | 8/2001 | Elliott et al. | 510/135 |
| 6,444,628 B2 | 9/2002 | Nocerino et al. | |
| 6,489,286 B1 | 12/2002 | Lukenbach et al. | |
| 6,494,920 B1 * | 12/2002 | Weuthen et al. | 8/137 |
| 6,514,918 B1 | 2/2003 | Librizzi | |
| 6,627,585 B1 * | 9/2003 | Steer | 510/120 |
| 2002/0128162 A1 * | 9/2002 | Elliott et al. | 510/130 |

FOREIGN PATENT DOCUMENTS

| | | |
|---|---|---|
| CA | 2001352 | 4/1990 |
| CA | 2094935 A1 | 4/1992 |
| CA | 2090137 A1 | 8/1993 |
| CA | 2141878 A1 | 2/1994 |
| CA | 1331550 C | 8/1994 |
| CA | 2180942 A1 | 8/1995 |
| CA | 2188877 A1 | 11/1995 |
| CA | 2190833 A1 | 2/1996 |
| CA | 2216964 A1 | 10/1996 |
| CA | 2221755 A1 | 11/1996 |
| CA | 2231809 A1 | 3/1997 |
| CA | 2191991 A1 | 6/1997 |
| CA | 2257810 A1 | 12/1997 |
| CA | 2276681 A1 | 7/1998 |
| CA | 2291274 A1 | 12/1998 |
| CA | 2306816 A1 | 4/1999 |
| CA | 2311510 A1 | 6/1999 |
| CA | 2275285 A1 | 12/1999 |
| CA | 2333317 A1 | 9/2000 |
| CA | 2290278 A1 | 5/2001 |
| DE | 4330597 A1 | 3/1995 |
| EP | 0 194 097 A | 9/1986 |
| EP | 0 194 097 A | 9/1988 |
| EP | 0 770 382 A | 5/1997 |
| EP | 1 136 066 A | 8/2001 |
| EP | 1 136 066 A | 9/2001 |
| JP | 7002677 A | 1/1995 |
| WO | WO 95 00116 A | 1/1995 |
| WO | WO 95 00118 A | 1/1995 |
| WO | WO 97/47171 A1 | 12/1997 |
| WO | WO 99 19438 A | 4/1999 |
| WO | WO 03 037283 A | 5/2003 |
| WO | WO 03 037293 A | 5/2003 |

OTHER PUBLICATIONS

EPO Search Report Dated Aug. 4, 2003, for EPO Appl. No. 02 25 5703 (JBP561EP).

EPO Search Report Dated Aug. 12, 2003, for EPO Appl. No. EP 02 25 5693 (JBP568EP).

* cited by examiner

Primary Examiner—Gregory R. Del Cotto

(57) ABSTRACT

A moisturizing detergent composition that is mild to the skin and eyes is disclosed. The composition includes a cationic polymer, a monoester emollient, a di-and/or tri-ester emollient and a surfactant. The compositions are useful as shampoos, washes, baths, gels, lotions, creams, and the like.

31 Claims, No Drawings

MOISTURIZING DETERGENT COMPOSITIONS

BACKGROUND OF THE INVENTION

1. Field of the Invention

The present invention relates to a mild moisturizing detergent composition having superior cleansing and moisturizing performance as well as low skin and ocular irritancy effects.

2. Description of the Prior Art

Historically, moisturizing cleansers have incorporated oils or silicones as the primary means for providing moisturization to hair and skin. See, e.g., U.S. Pat. No. 5,085,857 (silicone gums); and U.S. Pat. No. 6,194,364 (nonpolar oils or silicones in cleansing emulsion). However, because such ingredients tend to reduce the viscosity of the product and suppress its foamability, these moisturizing cleansers are not aesthetically preferred by customers.

One known method for overcoming these deleterious effects of the oils and silicones is to increase the concentration of the surfactants in the cleansing product. Although the resulting products possess the high foaming aesthetics preferred by customers, such products disadvantageously are not mild, do not effectively deposit the silicone and oil onto the skin, and further enhance the drying of the skin. Attempts have been made to overcome the detrimental effects of oils and silicones in a cleansing system by separating the oils and silicones from the cleansing system. See e.g., U.S. Pat. No. 5,612,307. While this approach may minimize the aforementioned negative effects associated with oils and silicones, it created an additional need for a two compartment packaging, which is not only expensive but also complicated to manufacture.

Therefore, there is a need for a moisturizing detergent that not only provides superior skin moisturization, but also is capable being viscosified easily, provides consumer acceptable levels of foam, and does not require complicated packaging. There is further a need for such a moisturizing detergent that would not compromise the mildness and safety properties of the overall cleansing composition.

SUMMARY OF THE INVENTION

It has been discovered that the aforementioned objectives can be achieved by the moisturizing detergent composition of the present invention comprising, consisting of, and/or consisting essentially of:
a. a cationic polymer;
b. an emollient selected from the group consisting of a diester, a triester, or a mixture thereof;
c. a monoester emollient; and
d. a cleansing surfactant.

Another embodiment of the present invention is directed to a moisturizing detergent composition comprising, consisting of, and/or consisting essentially of, based upon the total weight of the composition,
a. from about 0.01 percent to about 5 percent of guar hydroxypropyltrimonium chloride and/or polyquaternium 10;
b. from about 0.1 percent to about 5 percent of di-PPG-2 myreth-10 adipate;
c. from about about 0.1 percent to about 5 percent of a glyceryl ester; and
d. from about 0.5 percent to about 50 percent a cleansing surfactant.

We have unexpectedly found that the moisturizing detergent compositions of the present invention not only provide superior skin cleansing and moisturization, but also are capable of viscosity building and foam boosting without compromising the mildness and safety properties of the overall cleansing composition.

DETAILED DESCRIPTION OF PREFERRED EMBODIMENTS

The moisturizing detergent composition of the present invention is comprised of, consists of, and/or consists essentially of, based upon the total weight of the composition, from about 0.01 percent to about 5 percent, e.g. from about 0.01 percent to about 3 percent or from about 0.01 percent to about 2 percent of a cationic polymer; from about 0.1 percent to about 5 percent, e.g. from about 0.5 percent to about 3 percent, or from about 0.1 percent to about 2.5 percent of an emollient selected from the group consisting of a diester, a triester, or a mixture thereof; from about 0.1 percent to about 10 percent, e.g. from about 0.5 percent to about 5 percent or from about 0.75 percent to about 3 percent of a monoester emollient; and from about 0.5 percent to about 50 percent, e.g. from about 5 percent to about 15 percent, of a cleansing surfactant.

Cationic polymers that are suitable for use in the composition of the present invention include, but are not limited to those having a high molecular weight ranging from about 2,000 to about 5,000,000, e.g. from about 5,000 to about 3,000,000 or from about 100,000 to about 1,000,000.

Representative classes of suitable cationic polymers include, but are not limited to cationic polysaccharides; cationic homopolymers and copolymers derived from acrylic and or methacrylic acid; cationic cellulose resins; cationic copolymers of dimethyldiallylammonium chloride and acrylamide and/or acrylic acid; cationic homopolymers of dimethyldiallylammonium chloride; cationic polyalkylene and ethoxypolyalkylene imines; quaternized silicones and copolymers and mixtures thereof.

For example, such cationic polymers include the cationic guar gums such as guar hydroxypropyltrimonium chloride, which is commercially available from Rhodia Incorporated, under the tradename, "Jaguar C17;" quaternized hydroxy ethyl cellulose ethers, which are commercially available from Amerchol Corporation under the tradename, "Ucare Polymer JR 400;" copolymers of acrylamide and dimethyidiallylammonium chloride ethers, which are also known as polyquaternium 7 and are commercially available from the Mcintyre Group Ltd. under the tradename, "Mackernium 007" or from Allied Colloids under the tradename "Salcare SC10;" copolymers of vinylpyrrolidone and quaternized branched vinylpyrrolidone, which are commercially available from BASF Corporation under the tradename, "Luviquat Care;" Polyquaternium-6, which is available commercially from Allied Colloids under the tradename, "Salcare SC30;" and copolymers and mixtures thereof.

Diester or triester emollients suitable for use in the present invention may be made via the known reaction of fatty alkoxylated esters with a straight, branched or aromatic polyol or poly acid to form a diester or triester of a straight, branched or aromatic polyol or poly acid. The diester or triester reactant is comprised of two or three fatty alkoxylated moieties, respectively, having the structure set forth in formula I.:

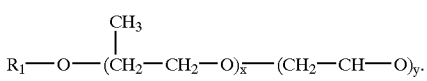

wherein:
- $R_1$ is a saturated or unsaturated, substituted or unsubstituted, straight, branched, or aromatic fatty moiety having a carbon chain length of from about 6 to about 30 atoms; and
- Each x and y are independently zero or an integer from 1 to 200, inclusive, with the proviso that the sum of x and y in each fatty alkoxylated moiety is independently between 1 and 300, inclusive, and the sum of all xs and ys in the diester or triester does not exceed 800.

The straight, branched, or aromatic polyol or polyacid is of the formula set forth in structure II.:

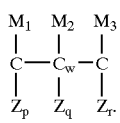

Wherein:
- $M_1$, $M_2$, and $M_3$ are independently a hydroxy, two single bonded hydrogens, or a double bonded oxygen;
- $Z_p$, $Z_q$, and $Z_r$ are independently hydrogen or a hydroxy;
- p, q, and r are independently zero or one, with the proviso that the sum of p+q+r is at least 2; and
- w is zero or an integer between 1 and 20, inclusive.

One suitable diester is Di-PPG-2 Myreth-10 Adipate, which is commercially available from Croda, Incorporated under the tradename, "Cromollient SCE," and has the structure set forth in formula III.:

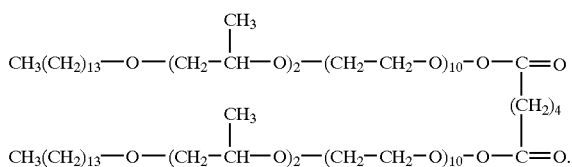

Monoester emollients suitable for use in the present invention include the esters made via the known reaction of a straight, branched or aromatic fatty acid having from about 4 carbon atoms to about 30 carbon atoms with a straight, branched or aromatic monohydric or polyhydric alcohol. If desired, the monohydric or polyhydric alcohol may be alkoxylated using known methods to improve its water solubility. The resulting monoester is of the structure set forth in formula IV.:

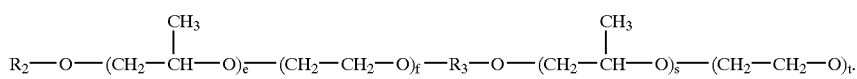

Wherein:

- $R_2$ is a saturated or unsaturated, substituted or unsubstituted straight, branched, or aromatic fatty moiety having a carbon chain length of from about 4 to about 30 atoms;
- $R_3$ is a saturated or unsaturated, substituted or unsubstituted, straight, branched, or aromatic monohydric or polyhydric alcohol having a carbon chain length from about 3 atoms to about 30 atoms; and
- Each e, f, s, and t are independently zero or integers from 1 to 100, inclusive, with the provisos that the sum of e and f is zero or an integer between 1 and 200, inclusive, that the sum of s and t is zero or an integer between 1 and 200, inclusive, and that the sum of e, f, s, and t does not exceed 400.

Examples of monoesters suitable for use in the present invention include the glyceryl esters, such as glyceryl oleate, which is commercially available from the Goldschmidt Chemical Corporation under the tradename, "Tegin O;" PEG-7 Glyceryl Cocoate, which is commercially available from Croda Incorporated under the tradename, "Glycerox HE;" and mixtures thereof.

In one embodiment, the HLB value of one or more of the di-/tri-ester emollients and monoester emollients is less than about 11, e.g. from about 2 to about 11 or from about 4 to about 11. In another embodiment, all of the di-/tri-ester emollients and the monoester emollients have an HLB value of less than about 11, e.g. from about 2 to about 11 or from about 4 to about 11.

Surfactants suitable for use in the present invention include those which are anionic, nonionic, amphoteric, betaine, or cationic, as well as mixtures thereof.

Classes of anionic surfactants useful in this invention include the alkyl sulfates, alkyl ether sulfates, sulfosuccinates, isethionates, acyl amides, alkyl ether carboxylates and alkyl phosphates, wherein the alkyl group has from about 6 carbon atoms to about 30 carbon atoms, with about 10 to about 14 carbon atoms being preferred.

Types of nonionic surfactants that are suitable for use in this invention include the fatty alcohol acid or amide ethoxylates, monoglyceride ethoxylates, sorbitan ester ethoxylates and alkyl polyglycosides.

Classes of amphoteric surfactants that are suitable for use in this invention include alkylimino-diproprionates, alkylamphoglycinates (mono or di), alkylamphoproprionates (mono or di), alkylamphoacetates (mono or di), N-alkyl β-aminoproprionic acids, alkylpolyamino carboxylates, and phosphorylated imidazolines.

Types of betaines that are suitable for use in this invention include alkyl betaines, alkylamido betaines, alkyl sultaines and alkylamido sultaines, wherein the alkyl group has from about 6 carbon atoms to about 30 carbon atoms, with about 10 to about 14 carbon atoms being preferred.

Classes of cationic surfactants that are suitable for use in this invention include alkyl quaternaries (mono, di, or tri), benzyl quaternaries, ester quaternaries, ethoxylated quaternaries, alkyl amines, and mixtures thereof, wherein the alkyl group has from about 6 carbon atoms to about 30 carbon atoms, with about 8 to about 22 carbon atoms being preferred.

The moisturizing cleanser compositions of the present invention may also include one or more optional ingredients nonexclusively including a pearlescent or opacifying agent, a thickening agent, humectants, chelating agents, and additives which enhance their appearance, feel and fragrance, such as colorants, fragrances, preservatives, pH adjusting agents, and the like. The pH of the mild cleansing compositions of this invention is preferably maintained in the range of from about 5 to about 7.5, and more preferably from about 5.5 to about 7.0.

Commercially available pearlescent or opacifying agents which are capable of suspending water insoluble additives and/or which tend to indicate to consumers that the resultant product is a moisturizing cleanser are suitable for use in this invention. The pearlescent or opacifying agent may be present in an amount, based upon the total weight of the composition, of from about 1 percent to about 10 percent, preferably from about 1.5 percent to about 7 percent, and more preferably, from about 2 percent to about 5 percent.

Examples of suitable pearlescent or opacifying agents include, but are not limited to mono or diesters of (a) fatty acids having from about 16 to about 22 carbon atoms and (b) either ethylene or propylene glycol; mono or diesters of (a) fatty acids having from about 16 to about 22 carbon atoms (b) a polyalkylene glycol of the formula: $HO-(JO)_a-H$, wherein J is an alkylene group having from about 2 to about 3 carbon atoms; and a is 2 or 3;fatty alcohols containing from about 16 to about 22 carbon atoms; fatty esters of the formula: $KCOOCH_2L$, wherein K and L independently contain from about 15 to about 21 carbon atoms; inorganic solids insoluble in the shampoo composition, and mixtures thereof The pearlescent or opacifying agent may be introduced to the mild cleansing composition as a pre-formed, stabilized aqueous dispersion, such as that commercially available from Henkel Corporation of Hoboken, New Jersey under the tradename, "Euperlan PK-3000." This material is a combination of glycol distearate (the diester of ethylene glycol and stearic acid), Laureth-4 ($CH_3(CH_2)_{10}CH_2(OCH_2CH_2)_4OH$) and cocamidopropyl betaine and preferably is in a weight percent ratio of from about 25 to about 30: about 3 to about 15: about 20 to about 25, respectively.

Commercially available thickening agents, which are capable of imparting the appropriate viscosity to the mild cleansing compositions are suitable for use in this invention. If used, the thickener should be present in the shampoo compositions in an amount sufficient to raise the Brookfield viscosity of the composition to a value of between about 500 to about 10,000 centipoise. Examples of suitable thickening agents nonexclusively include: mono or diesters of 1) polyethylene glycol of formula: $HO-(CH_2CH_2O)_zH$, wherein z is an integer from about 3 to about 200; and 2) fatty acids containing from about 16 to about 22 carbon atoms; fatty acid esters of ethoxylated polyols; ethoxylated derivatives of mono and diesters of fatty acids and glycerine; hydroxyalkyl cellulose; alkyl cellulose; hydroxyalkyl alkyl cellulose; and mixtures thereof. Preferred thickeners include polyethylene glycol ester, and more preferably PEG-150 distearate which is available from the Stepan Company of Northfield, Ill. or from Comiel, S.p.A. of Bologna, Italy under the tradename, "PEG 6000 DS".

Commercially available humectants, which are capable of providing moisturization and conditioning properties to the mild cleansing composition, are suitable for use in the present invention. The humectant may be present in an amount of from about 0 percent to about 10 percent, preferably from about 0.5 percent to about 5 percent, and more preferably from about 0.5 percent to about 3 percent, based on the overall weight of the composition. Examples of suitable humectants nonexclusively include: 1) water soluble liquid polyols selected from the group comprising glycerine, propylene glycol, hexylene glycol, butylene glycol, dipropylene glycol, and mixtures thereof; 2)polyalkylene glycol of the formula: $HO-(R"O)_b-H$, wherein R" is an alkylene group having from about 2 to about 3 carbon atoms and b is an integer of from about 2 to about 10; 3) polyethylene glycol ether of methyl glucose of formula $CH_3-C_6H_{10}O_5(OCH_2CH_2)_c-OH$, wherein c is an integer from about 5 to about 25; 4) urea; and 5) mixtures thereof, with glycerine being the preferred humectant.

Examples of suitable chelating agents include those which are capable of protecting and preserving the compositions of this invention. Preferably, the chelating agent is ethylenediamine tetracetic acid ("EDTA"), and more preferably is tetrasodium EDTA, available commercially from Dow Chemical Company of Midland, Mich. under the tradename, "Versene 100XL" and is present in an amount, based upon the total weight of the composition, from about 0 to about 0.5 percent, and preferably from about 0.05 percent to about 0.25 percent.

Suitable preservatives include Quaternium-15, available commercially as "Dowicil 200" from the Dow Chemical Corporation of Midland, Mich., and are present in the composition in an amount, based upon the total weight of the composition, from about 0 to about 2.0 percent, and preferably from about 0.05 percent to about 0.10 percent.

The compositions of the present invention are preferably used in personal care products such as shampoos, washes, baths, gels, lotions, creams, and the like.

In one embodiment, the composition may be incorporated into a bath fizz ball, such as those described in U.S. Pat. Nos. 4,650,661; 4,666,707; and 4,002,758; which are incorporated herein by reference.

The composition of the present invention may be used on the body in conjunction with any personal cleansing implement known in the art such as a washcloth, a mesh or apertured film, pouf, sponge, brush and the like. In one embodiment, the composition may be marketed together with one or more of such implements in a kit.

In one embodiment, the compositions of the present invention are "substantially free" of oils or silicones. As used herein, "substantially free" shall mean that the moisturizing cleanser composition contains, based upon the total weight of the composition, less than about 1 percent, for example, less than about 0.5 percent or less than about 0.2 percent oils and/or silicones.

The invention illustratively disclosed herein suitably may be practiced in the absence of any component, ingredient, or step which is not specifically disclosed herein. Several examples are set forth below to further illustrate the nature of the invention and the manner of carrying it out. However, the invention should not be considered as being limited to the details thereof.

EXAMPLES

Example 1

Preparation of Moisturizing Detergent Composition

The moisturizing detergent composition of Example 1 was prepared according to the materials and amounts listed in Table 1.:

TABLE 1

| Tradename/Supplier | INCI Name | % w/w |
|---|---|---|
| Plantaren 2000 from Cognis Corporation | Decyl Glucoside | 0.6 |
| Lamesoft P065 from Cognis Corporation | | 3.00 |
| | Water | 1.05 |
| | Coco glucoside | 1.05 |
| | Glyceryl oleate | 0.9 |
| PEG 6000 DS from Stepan Company | PEG 150 distearate | 1.4 |
| Atlas G4280 from Uniqema | POE 80 sorbitan laurate | 5.0 |
| Water | Deionized water | 59.67 |
| Polymer JR from Amerchol Corporation | Polyquaternium 10 | 0.12 |
| Glucquat 125 from Amerchol Corporation | Lauryl methyl gluceth-10 hydroxypropyldimonium chloride | 1.00 |
| Tegobetaine L-7 (30%) from Goldschmidt Chemical Corporation | Cocamidopropyl betaine | 12.00 |
| Monateric 949J from Uniqema | Disodium lauroamphodiacetate | 2.00 |
| Polyox WSR-205 from Amerchol Corporation | PEG 14-M | 0.10 |
| Glycerin from Cognis Corporation | Glycerin | 0.50 |
| Cromollient SCE from Croda Inc. | Di-PPG-Myreth-10-Adipate | 1.00 |
| Lipovol J from Lipo Chemicals, Inc. | Jojoba oil | 0.1 |
| Drakeol 7 from Penreco | Mineral oil | 0.10 |
| Fragrance | Fragrance | 0.50 |
| Dowicil 200 from Dow Chemical Company | Quaternium 15 | 0.05 |
| Versene 100XL from Dow Chemical Company | Tetrasodium EDTA | 0.46 |
| Euperlan PK 3000 from Cognis Corporation | | 2.00 |
| | Cocamidopropyl betaine | |
| | Glycol distearate | |
| | Laureth-4 | |
| Citric acid (20%) | Citric acid | As needed |

The composition of Example 1 was prepared as follows:

The following Pre-Mixtures were prepared:

Pre-Mixture 1: PEG-14M and glycerin were mixed in an independent container under ambient conditions.

Pre-Mixture 2: Di-PPG-2-myreth-10-adipate, mineral oil, and jojoba oil were mixed in an independent container under ambient conditions.

Pre Mixture 3: The fragrance and 1 part of POE-80 sorbitan laurate were mixed in an independent container under ambient conditions.

Component amounts in this procedure are given in terms of parts by weight of active to prepare 100 parts of the cleansing composition.

The decyl glucoside, cocoglucoside, and glyceryl oleate were mixed in an independent container under ambient conditions until the resulting solution was clear. The solution was then heated to a temperature of about 50° C. to 55° C. with constant stirring. PEG 150 distearate was added thereto with stirring at constant temperature until the PEG 150 distearate was dissolved therein. As the resulting solution was cooled to 40° C., the following components were added thereto sequentially with stirring, and the solution was homogeneous before the addition of each subsequent component: (4 parts) POE-80 sorbitan laurate; (59.67 parts) water; polyquaternium-10; lauryl methyl gluceth-10 hydroxypropyidimonium chloride; cocamidopropylbetaine; disodium lauroamphodiacetate; PEG-14M/glycerin pre-mix; and Di-PPG-2-myreth-10-adipate/mineral oil/jojoba oil pre-mix.

After the resulting mixture was cooled to a temperature of about 40° C., the following components were added thereto sequentially, and the solution was homogeneous before the addition of each subsequent component: fragrance/POE-80 sorbitan laurate premixture, quaternium-15, tetrasodium EDTA, glycol distearate, and laureth-4. After sodium chloride was added thereto, the pH of the resulting solution was adjusted with citric acid to about 6.8. The remaining water was added thereto with stirring until the final solution was homogeneous.

The viscosity of the resulting solution was 1300 cps as measured by a Brookfield DV-I+ Viscometer using a # 2 spindle and speed of 6 rpm.

Example 2

Preparation of Moisturizing Detergent Composition

The moisturizing detergent composition of Example 2 was prepared according to the materials and amounts listed in Table 2.:

TABLE 2

| Tradename/Supplier | INCI Name | % w/w |
|---|---|---|
| Lamesoft P065 | | 3.00 |
| | Water | 1.05 |
| | Coco glucoside | 1.05 |
| | Glyceryl oleate | 0.9 |
| PEG 6000 DS | PEG 150 distearate | 1.0 |
| Atlas G4280 | POE 80 sorbitan laurate | 5.0 |
| Water | Deionized water | 65.69 |
| Polymer JR | Polyquaternium 10 | 0.10 |
| Glucquat 125 | Lauryl methyl gluceth-10 hydroxypropyldimonium chloride | 1.00 |
| Tegobetaine L-7 (30%) | Cocamidopropyl betaine | 8.00 |
| Monateric 949J | Disodium lauroamphodiacetate | 2.00 |
| Polyox WSR-205 | PEG 14-M | 0.05 |
| Glycerin | Glycerin | 0.50 |
| Cromollient SCE | Di-PPG-Myreth-10-Adipate | 1.00 |
| Jaguar C17 from Rhodia, Inc | Guar hydroxypropyltrimonium chloride | 0.1 |
| Dowicil 200 | Quaternium 15 | 0.05 |
| Versene 100XL | Tetrasodium EDTA | 0.506 |
| Rhodapex from Rhodia, Inc. | Sodium Laureth-2 Sulfate | 10.00 |
| Euperlan PK 3000 | | 2.00 |
| | Cocamidopropyl betaine | |
| | Glycol distearate | |
| | Laureth-4 | |
| Sodium hydroxide solution (20%) | Sodium hydroxide | As needed |
| Citric acid (20%) solution | Citric acid | As needed |

The composition of Example 2 was prepared as follows:

The following Pre-Mixtures were prepared:

Pre-Mixture 1: PEG-14M and glycerin were mixed in an independent container under ambient conditions.

Component amounts in this procedure are given in terms of parts by weight of active to prepare 100 parts of the cleansing composition.

Guar hydroxypropyltrimonium chloride and polyquaternium 10 were added to a beaker containing (65.59 parts) water with stirring under ambient conditions until dissolved. After heating the solution to 50° C., PEG 150 distearate was stirred therein at constant heat until dissolved. As the resulting solution was cooled to 40° C., the lauryl methyl gluceth-10 hydroxypropyidimonium chloride was added thereto with mixing until homogeneous. The following components were then added thereto sequentially with stirring, and the solution was homogeneous before the addition of each subsequent component: POE-80 sorbitan laurate; cocamidopropylbetaine; disodium lauroamphodiacetate; sodium laureth-2 sulfate; coco glucoside and glyceryl oleate; Di-PPG-2-myreth-10-adipate; and PEG-14M/glycerin pre-mix.

After the resulting mixture was cooled to a temperature of about 40° C., the following components were added thereto sequentially, and the solution was homogeneous before the addition of each subsequent component: quaternium-15, tetrasodium EDTA, glycol distearate and laureth-4. The pH of the resulting solution was adjusted with citric acid and sodium hydroxide to about 6.25 to about 7.25. The remaining water was added thereto with stirring until the final solution was homogeneous.

The viscosity of the resulting solution was 18,500 cps as measured by a Brookfield DV-I+ Viscometer using a # 2 spindle and speed of 15 rpm.

Example 3

Preparation of Moisturizing Detergent Composition

The moisturizing detergent composition of Example 3 was prepared according to the materials and amounts listed in Table 3.:

TABLE 3

| Tradename/Supplier | INCI Name | % w/w |
| --- | --- | --- |
| Plantaren 2000 | Decyl Glucoside | 6.00 |
| Glycerox HE from Croda Inc. | PEG 7 glyceryl cocoate (having HLB of 10.6) | 1.00 |
| PEG 6000 DS | PEG 150 distearate | 1.4 |
| Atlas G4280 | POE 80 sorbitan laurate | 5.0 |
| Water | Deionized water | 61.67 |
| Polymer JR | Polyquaternium 10 | 0.12 |
| Glucquat 125 | Lauryl methyl gluceth-10 hydroxypropyldimonium chloride | 1.00 |
| Tegobetaine L-7 (30%) | Cocamidopropyl betaine | 12.00 |
| Monateric 949J | Disodium lauroamphodiacetate | 2.00 |
| Polyox WSR-205 | PEG 14-M | 0.10 |
| Glycerin | Glycerin | 0.50 |
| Cromollient SCE | Di-PPG-Myreth-10-Adipate | 1.00 |
| Lipovol J | Jojoba oil | 0.1 |
| Drakeol 7 | Mineral oil | 0.10 |
| Fragrance | Fragrance | 0.50 |
| Dowicil 200 | Quaternium 15 | 0.05 |
| Versene 100XL | Tetrasodium EDTA | 0.46 |
| Euperlan PK 3000 | Cocamidopropyl betaine Glycol distearate Laureth-4 | 2.00 |
| Sodium chloride | Sodium chloride salt | 5.00 |
| Citric acid (20%) | Citric acid | As needed |

The composition of Example 3 was prepared as follows:

The following Pre-Mixtures were prepared:

Pre-Mixture 1:4 parts POE 80 sorbitan laurate, decyl glucoside, and PEG 7 glyceryl cocoate were mixed in an independent container under ambient conditions until clear.

Pre-Mixture 2: Di-PPG-2-myreth-10-adipate, mineral oil, and jojoba oil were mixed in an independent container under ambient conditions.

Pre Mixture 3: The fragrance and 1 part of POE-80 sorbitan laurate were mixed in an independent container under ambient conditions.

Pre-Mixture 4: The PEG 14M and glycerin were mixed in an independent container under ambient conditions.

Component amounts in this procedure are given in terms of parts by weight of active to prepare 100 parts of the cleansing composition.

After heating the pre-mixture 1 to a temperature of about 50° C. to 55° C. with constant stirring, PEG 150 distearate was added thereto with stirring at constant temperature until the PEG 150 distearate was dissolved therein. After the resulting solution was removed from the heat, the following components were added thereto sequentially with stirring, and the solution was homogeneous before the addition of each subsequent component: (61.67 parts) water; polyquaternium-10; lauryl methyl gluceth-10 hydroxypropyldimonium chloride; cocamidopropylbetaine; disodium lauroamphodiacetate; PEG-14M/glycerin pre-mix; and Di-PPG-2-myreth-10-adipate/mineral oil/jojoba oil pre-mix.

After the resulting mixture was cooled to a temperature of about 40° C., the following components were added thereto sequentially, and the solution was homogeneous before the addition of each subsequent component: fragrance/POE-80 sorbitan laurate premixture, quaternium-15, tetrasodium EDTA, and glycol distearate/laureth-4 mixture. After sodium chloride was added thereto, the pH of the resulting solution was adjusted with citric acid to about 6.8. The remaining water was added thereto with stirring until the final solution was homogeneous.

The viscosity of the resulting solution was 405 cps as measured by a Brookfield DV-I+ Viscometer using a # 2 spindle and speed of 6 rpm.

Example 4

Preparation of Moisturizinq Detergent Composition

The moisturizing detergent composition of Example 4 was prepared in accordance with the procedure set forth in Example 3 using the materials and amounts listed in Table 3, with the exception that the "Glycerox HE" was substituted with an equivalent amount of PEG 6 caprylic/capric glycerides, which is commercially available from Croda Incorporated_under the tradename, "Glycerox 767" and has an HLB value of 13.2.

The viscosity of the resulting solution was 145 cps as measured by a Brookfield DV-I+ Viscometer using a # 2 spindle and speed of 6 rpm.

Example 5

Comparison of Moisturizinq Detergent Composition With Commercial Products

Three hundred female consumer panelists who have previously used moisturizing cleanser compositions participated in a blind comparative study between the composition produced in accordance with Example 2, as well as five other commercially available cleansers: 1) "Cetaphil_ Gentle Skin Cleanse available from Galderma Laboratories, Incorporated; 2) "Aveeno Baby Cleanser" available from Johnson & Johnson Consumer Companies, Inc., 3) "Purpose Gentle Cleansing Wash" available from Johnson & Johnson Consumer Companies, Inc., 4) "Oil of Olay Sensitive Skin Foaming Facial Wash" available from the Procter and Gamble Company; and 5) "RoC Enydrial Foaming Gel" available from Johnson & Johnson Consumer Companies, Inc.

During the study, the panelists were divided into six groups of 50 participants. Each group was assigned one of the six above mentioned products, then asked to wash their faces with that product at least 5 times a week for a total of 2 weeks. At the end of the study, each panelist completed a questionnaire regarding the benefits of using the product. The results of the questionnaires are set forth in Tables 4, 5, and 6 below:

TABLE 4

Key Directionals From Panelist Questionnaires

|  | NON-FOAMING | | FOAMING | | | |
|---|---|---|---|---|---|---|
|  | | | Moisturizing | Purpose Gentle | Oil of Olay | |
|  | Cetaphil (A) | Aveeno Baby Cleanser (B) | Cleanser of Ex 2 (C) | Cleansing Wash (D) | Foaming Face Wash (E) | ROC Endrial Foaming Gel (F) |
| KEY DIRECTIONALS ON QUESTIONNAIRE: | | | | | | |
| CONSISTENCY - "Just About Right" | 36% | 60%A | 86%A*Bd** | 72%A | 78%Ab | 76%Ab |
| AMOUNT OF LATHER - 11 pt | 2.96 | 3.50 | 6.70ABE | 6.10AB | 5.68AB | 6.58ABe |
| AMOUNT OF LATHER - "Just About Right" | 32% | 42% | 72%ABd | 54%A | 66%AB | 62%AB |
| LATHER CONSISTENCY - 10 pt | n/a | n/a | 6.80DEF | 5.50 | 5.52 | 5.48 |
| LIKING OF LATHER CONSISTENCY - 5pt | n/a | n/a | 4.06d | 3.52 | 3.68 | 3.66 |
| LATHER TEXTURE - 10 pt | n/a | n/a | 7.04D | 6.20 | 6.66 | 6.50 |
| LIKING OF LATHER TEXTURE - 5 Pt | n/a | n/a | 3.94 | 3.62 | 3.66 | 3.76 |
| EASE OF RINSING - 5 pt | 4.14 | 4.20 | 4.38 | 4.20 | 4.16 | 4.04 |
| EASE OF WIPING - 5 pt | 4.20 | 4.20 | n/a | n/a | n/a | n/a |
| MOISTURIZED SKIN FEEL AFTER USE | | | | | | |
| Very Moisturized | 48%D | 36% | 40% | 26% | 36% | 42%d |
| Somewhat Moisturized | 44% | 54% | 50% | 60% | 56% | 46% |
| Not at All Moisturized | 8% | 10% | 10% | 14% | 8% | 12% |
| DRY/TIGHT SKIN FEEL AFTER USE | | | | | | |
| Very Dry or Tight | 0% | 2% | 4% | 4% | 4% | 2% |
| Somewhat Dry or Tight | 12% | 6% | 22%B | 28%AB | 20%B | 20%B |
| Not At All Dry or Tight | 88%cDe | 92%CDEf | 74% | 68% | 74% | 78% |
| CLEANSER USED TO REMOVE MAKEUP | | | | | | |
| Yes | 80%e | 78%e | 74% | 74% | 62% | 72% |
| No | 20% | 22% | 26% | 26% | 38%ab | 28% |
| REMOVING MAKEUP - 10 pt | 7.38 | 6.97 | 8.51ABE | 8.03B | 7.58 | 8.42ABe |
|  | (n = 40) | (n = 39) | (n = 37) | (n = 37) | (n = 31) | (n = 36) |
| EASE OF REMOVING MAKEUP - 10 pt | 7.55 | 7.00 | 8.54AB | 8.05b | 7.84 | 8.42aB |

TABLE 5

Panelists "Agree Completely/Somewhat" With Listed Benefits

|  | NON-FOAMING | | FOAMING | | | |
|---|---|---|---|---|---|---|
|  | | | Moisturizing | Purpose Gentle | Oil of Olay | |
| AGREE COMPLETELY/SOMEWHAT - Top 2 Box | Cetaphil (A) | Aveeno Baby Cleanser (B) | Cleanser of Ex 2 (C) | Cleansing Wash (D) | Foaming Face Wash (E) | ROC Endrial Foaming Gel (F) |
| END BENEFITS | | | | | | |
| Is an Effective Cleanser | 78% | 74% | 94%ABe | 90%B | 82% | 92%aB |
| Cleans & Moisturizes At The Same Time | 78% | 78% | 88% | 78% | 80% | 86% |
| Cleans Without Drying Skin | 86% | 88% | 90% | 80% | 88% | 86% |
| Leaves Skin Soft & Smooth | 84% | 80% | 88% | 84% | 84% | 88% |
| Does Not Clog Pores | 72% | 80% | 92%AbF | 82% | 82% | 72% |
| Helps Skin Look & Feel Healthier | 72% | 74% | 94%ABDEF | 78% | 80% | 74% |
| Helps to Even Out Blotchy & Uneven Skin Tone | 34% | 54% | 60%A | 52%a | 50% | 48% |
| Leaves Skin Feeling Clean | 76% | 72% | 96%ABe | 92%AB | 86%b | 92%AB |
| Leaves Skin Feeling Refreshed | 76% | 72% | 92%ABc | 84% | 80% | 82% |
| Helps Unclog Pores | 52% | 58% | 78%ABdef | 62% | 60% | 60% |
| Smoothes Rough, Uneven Patches | 44% | 48% | 70%ABDE | 50% | 48% | 64%A |
| Helps to Improve Skin Texture | 54% | 60% | 84%ABDE | 66% | 62% | 72%a |
| Provides Long Lasting Moisture | 66% | 64% | 82%aBd | 66% | 76% | 72% |
| Soothes Dry Skin | 72% | 64% | 84%BD | 66% | 76% | 82%Bd |
| Adds Moisture Back to The Skin | 68% | 64% | 86%AB | 74% | 74% | 78% |
| AMONG WOMEN WHO USED THE PRODUCT TO REMOVE | | | | | | |
| MAKEUP | (n = 40) | (n = 39) | (n = 37) | (n = 37) | (n = 31) | (n = 36) |
| Removes Makeup & Cleanses in One Step | 80% | 77% | 100%ABDE | 86% | 87% | 94%aB |
| Removes Foundation or Base Makeup | 88% | 85% | 97%bd | 86% | 90% | 89% |

TABLE 5-continued

Panelists "Agree Completely/Somewhat" With Listed Benefits

| | NON-FOAMING | | FOAMING | | | |
| | | | Moisturizing | Purpose Gentle | Oil of Olay | |
| AGREE COMPLETELY/SOMEWHAT - Top 2 Box | Cetaphil (A) | Aveeno Baby Cleanser (B) | Cleanser of Ex 2 (C) | Cleansing Wash (D) | Foaming Face Wash (E) | ROC Endrial Foaming Gel (F) |
|---|---|---|---|---|---|---|
| Removes Eye Makeup | 70% | 69% | 76% | 76% | 81% | 83% |
| PRODUCT CHARACTERISTICS: | | | | | | |
| Is Good for Even Very Dry Skin | 84%d | 80% | 82% | 70% | 78% | 84%d |
| Is a Product for Someone Like Me | 60% | 70% | 86%Abf | 78%a | 78%a | 72% |
| Is Not Irritating to Your Skin | 90% | 92% | 98%Adf | 90% | 92% | 88% |
| Is Good for Use Everyday | 84% | 90% | 96%Ae | 90% | 86% | 90% |
| Is Pleasant to Use | 66% | 78% | 90%AF | 86%Af | 86%Af | 70% |
| Has A Good Consistency or Thickness | 36% | 62%A | 86%ABf | 80%Ab | 80%Ab | 72%A |
| Is Not Irritating to Eyes | 80% | 92%af | 96%ADEF | 84% | 84% | 78% |
| Rinses Off Easily & Completely | 86% | 82% | 96%aBEF | 88% | 84% | 78% |
| Leaves No Unpleasant Residue On Skin | 82% | 80% | 96%ABE | 94%aBE | 76% | 88% |
| Is Good For Sensitive Skin | 78% | 70% | 88%Bd | 74% | 82% | 82% |
| Gentle to Skin | 92% | 92% | 96%E | 90% | 84% | 90% |
| Moisturizes Better Than Other Cleansers | 62% | 60% | 84%ABDef | 62% | 68% | 70% |
| Is a High Quality Product | 60% | 64% | 88%ABdF | 74% | 76%a | 68% |
| Is Fragrance Free | 86%cDEF | 76%D | 72%d | 54% | 68% | 64% |
| Wipes Off Easily & Completely | 82% | 84% | n/a | n/a | n/a | n/a |
| END BENEFITS: | | | | | | |
| Is An Effective Cleanser | 48% | 44% | 74%ABEf | 60% | 54% | 56% |
| Cleans & Moisturizes At The Same Time | 56% | 46% | 66%BE | 50% | 46% | 50% |
| Cleans Without Drying Skin | 56% | 56% | 62% | 56% | 54% | 50% |
| Leaves Skin Soft & Smooth | 58% | 50% | 60% | 48% | 58% | 58% |
| Does Not Clog Pores | 42% | 40% | 64%ABF | 56% | 54% | 44% |
| Helps Skin Look & Feel Healthier | 28% | 40% | 64%ABD | 42% | 54%A | 50%A |
| Helps to Even Out Blotchy & Uneven Skin Tone | 10% | 24%a | 22% | 16% | 22% | 20% |
| Leaves Skin Feeling Clean | 44% | 44% | 76%ABef | 64%AB | 60% | 60% |
| Leaves Skin Feeling Refreshed | 48% | 46% | 70%ABD | 50% | 54% | 54% |
| Helps Unclog Pores | 18% | 32% | 40%Ad | 22% | 28% | 36%A |
| Smoothes Rough, Uneven Patches | 12% | 20% | 38%Abe | 24% | 20% | 30%A |
| Helps to Improve Skin Texture | 22% | 30% | 46%Ad | 28% | 34% | 44%Ad |
| Provides Long Lasting Moisture | 30% | 30% | 46% | 38% | 42% | 40% |
| Soothes Dry Skin | 28% | 38% | 48%A | 44a % | 38% | 44%a |
| Adds Moisture Back to The Skin | 22% | 38a % | 52% | 40a % | 38a % | 46%A |
| AMONG WOMEN WHO USED THIS PRODUCT TO REMOVE MAKEUP | (n = 40) | (n = 39) | (n = 37) | (n = 37) | (n = 31) | (n = 36) |
| Removes Makeup & Cleanses in One Step | 48% | 38% | 70%AB | 57% | 55% | 56%a |
| Removes Foundation or Base Makeup | 55%B | 31% | 68%B | 59%B | 61%B | 56%B |
| Removes Eye Makeup | 50%b | 28% | 54%B | 49%b | 45% | 50%b |
| PRODUCT CHARACTERISTICS | | | | | | |
| Is Good for Even Very Dry Skin | 42% | 42% | 56%D | 34% | 40% | 44% |
| Is a Product for Someone Like Me | 36% | 42% | 62%ABD | 36% | 46% | 46% |
| Is Not Irritating to Your Skin | 74% | 62% | 74% | 72% | 72% | 62% |
| Is Good for Use Everyday | 66% | 62% | 74%f | 74%f | 62% | 58% |
| Is Pleasant to Use | 40% | 52% | 56%f | 54% | 58%aF | 38% |
| Has A Good Consistency or Thickness | 18% | 30% | 62%ABD | 38%A | 46%A | 46%A |
| Is Not Irritating to Eyes | 46% | 58% | 69%Af | 68%Af | 54% | 50% |
| Rinses Off Easily & Completely | 56% | 48% | 66%b | 66%b | 58% | 52% |
| Leaves No Unpleasant Residue On Skin | 60% | 52% | 78%aBEF | 70%bF | 54% | 50% |
| Is Good For Sensitive Skin | 38% | 38% | 62%AB | 50% | 50% | 48% |
| Gentle to Skin | 48% | 50% | 72%ABE | 60% | 62% | 50% |
| Moisturizes Better Than Other Cleansers | 30% | 28% | 42% | 28% | 28% | 34% |
| Is a High Quality Product | 26% | 36% | 54%Ab | 40% | 42%a | 40% |
| Is Fragrance Free | 56%d | 46% | 44% | 38% | 44% | 44% |
| Wipes Off Easily & Completely | 54% | 42% | n/a | n/a | n/a | n/a |

TABLE 6

Comparison to Brand Used Most Often

| | NON-FOAMING | | FOAMING | | | |
| --- | --- | --- | --- | --- | --- | --- |
| | | | Moisturizing | Purpose Gentle | Oil of Olay | |
| | Cetaphil (A) | Aveeno Baby Cleanser (B) | Cleanser of Ex 2 (C) | Cleansing Wash (D) | Foaming Face Wash (E) | ROC Endrial Foaming Gel (F) |
| COMPARED TO BRAND USED MOST OFTEN. | | | | | | |
| LEAVING SKIN SOFT & SMOOTH - 5 pt | 3.42d | 3.22 | 3.54D | 3.08 | 3.34 | 3.34 |
| PROVIDING LONG LASTING MOISTURIZATION - 5 pt | 3.24 | 3.20 | 3.56bD | 3.04 | 3.32 | 3.34 |
| LEAVING SKIN FEELING CLEAN - 5pt | 3.08 | 2.92 | 3.66ABDe | 3.18 | 3.28b | 3.48aB |
| BEING GOOD FOR EVEN VERY DRY SKIN - 5pt | 3.34 | 3.38 | 3.74abDE | 3.12 | 3.24 | 3.44 |
| CLEANSING & MOISTURIZING AT THE SAME TIME - 5 Pt | 3.48 | 3.28 | 3.82BD | 3.30 | 3.46 | 3.54 |
| RELIEVING DRY SKIN - 5 pt | 3.28 | 3.30 | 3.72ABDE | 3.08 | 3.22 | 3.42 |
| LEVEL OF SKIN IRRITATION: | | | | | | |
| Extremely Irritating | 2% | 0% | 0% | 0% | 0% | 0% |
| Very Irritating | 0% | 0% | 0% | 0% | 2% | 0% |
| Somewhat Irritating | 2% | 0% | 0% | 2% | 2% | 4% |
| Slightly Irritating | 4% | 2% | 0% | 4% | 4% | 4% |
| Not at All Irritating | 92% | 98% | 100%AdEF | 94% | 92% | 92% |
| UNPLEASANT EYE REACTIONS | | | | | | |
| Yes | 2% | 2% | 2% | 2% | 4% | 2% |
| No | 98% | 98% | 98% | 98% | 96% | 98% |
| LEVEL OF EYE IRRITATION: | | | | | | |
| Extremely Irritating | 0% | 0% | 0% | 0% | 0% | 0% |
| Very Irritating | 0% | 0% | 2% | 0% | 2% | 0% |
| Somewhat Irritating | 2% | 2% | 0% | 0% | 0% | 2% |
| Slightly Irritating | 0% | 2% | 2% | 2% | 4% | 2% |
| Not at All Irritating | 98% | 96% | 96% | 98% | 94% | 96% | a capital letter represents that the value given for the cleanser of that column is at a 95 degree confidence level with respect to the value given for the cleanser denoted by the capital letter. For example, "86% ABd" means that the 86% value is accurate to a 95% confidence level with respect to the values for the cleansers of columns A and B.

a lowercase letter represents that the value given for the cleanser of that column is at a 90 degree confidence level with respect to the value given for the cleanser denoted by the capital letter. For example, "86% ABd" means that the 86% value is accurate to a 90% confidence level with respect to the value for the cleansers of column d.

This Example showed that the moisturizing detergent composition of the present invention was superior with respect to cleansing, moisturizing, and improving healthy look and feel of skin, while remaining very gentle to skin and eyes. This Example further showed that the moisturizing detergent composition of the present invention was an effective eye and face make-up remover.

We claim:

1. A moisturizing detergent composition comprising:
   a. a cationic polymer;
   b. a diester, wherein the diester is di-PPG-2 myreth-10 adipate;
   c. a monoester emollient; and
   d. a cleansing surfactant.

2. The composition of claim 1 comprising, based upon the total weight of the composition,
   a. from about 0.01 percent to about 5 percent of said cationic polymer;
   b. from about 0.1 percent to about 5 percent of said di-PPG-2 myreth-10 adinate;
   c. from about 0.1 percent to about 5 percent of said monoester emollient; and
   d. from about 0.5 percent to about 50 percent of said cleansing surfactant.

3. The composition of claim 1 comprising, based upon the total weight of the composition,
   a. from about 0.01 percent to about 2 percent of said cationic polymer;
   b. from about 1 percent to about 2.5 percent of said di-PPG-2 myreth-10 adipate;
   c. from about about 0.5 percent to about 3 percent of said monoester emollient; and
   d. from about 5 percent to about 15 percent of said cleansing surfactant.

4. The composition of claim 1 wherein the cationic polymer is selected from the group consisting of cationic polysaccharides; cationic homopolymers derived from acrylic and/or methacrylic acid; copolymers derived from acrylic and/or methacrylic acid; cationic cellulose resins; cationic copolymers of dimethyldiallylamnionium chloride and acrylamide and/or acrylic acid; catiome hornopolymers of dimethyldiallylammonium chloride; cationic polyalkylene imines; cationic ethoxypolyalkylene imines; quaternized silicones; and copolymers and mixtures thereof.

5. The compositions of claim 4 wherein the cationic polymer is a cationic guar gum, a quaternized hydroxyethyl cellulose ether, a copolymer of acrylamide and dimethyldiallylanimonium chloride ether, a copolymer of vinyl pyrrolidone and quaternized branched vinylpyrrolidone, and copolymers and mixtures thereof.

6. The composition of claim 5 wherein the cationic polymer is guar hydroxypropyltrimonium chloride, polyquaternium 10, and copolymers and mixtures thereof.

7. The composition of claim 1, wherein the monoester results from the reaction of a fatty acid moiety having a carbon chain length of from about 4 carbon atoms to about 30 carbon atoms with a monohydric or polyhydric alcohol.

8. The composition of claim 7, wherein the monoester is of the structure IV.:

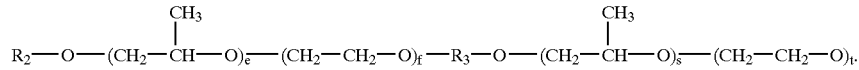

IV

Wherein:
- $R_2$ is a saturated or unsaturated, substituted or unsubstitued straight, branched, or aromatic fatty moiety having a carbon chain length of from about 4 to about 30 atoms;
- $R_3$ is a saturated or unsaturated, substituted or unsubstituted, straight, branched, or aromatic monohydric or polyhydric alcohol having a carbon chain length from about 3 atoms to about 30 atoms;
- Each e, f, s, and t are independently zero or integers from 1 to 100, inclusive, with the provisos that the sum of e and f is zero or an integer between 0 and 200, inclusive, that the sum of s and t is zero or an integer between 0 and 200, inclusive, and that the sum of e, f, s, and t does not exceed 400.

9. The composition of claim 8, wherein the monoester is a glyceryl ester.

10. The composition of claim 9, wherein the glyceryl ester is selected from the group consisting of glyceryl oleate, PEG-7 glyceryl cocoate, and mixtures thereof.

11. The composition of claim 1, wherein the surfactant is selected from the group consisting of anionic, nonionic, amphoteric, betaine, cationic, and mixtures thereof.

12. The composition of claim 11, wherein the anionic surfactant is selected from the group consisting of alkyl sulfates, alkyl ether sulfates, sulfosuccinates, isethionates, acyl amides, alkyl ether carboxylates, alkyl phosphates, and mixtures thereof.

13. The composition of claim 11, wherein the nonionic surfactant is selected from the group consisting of fatty alcohol acid ethoxylates, fatty alcohol amide ethoxylates, monoglyceride ethoxylates, sorbitan ester ethoxylates, alkyl polyglycosides, and mixtures thereof.

14. The composition of claim 11 wherein the amphoteric surfactant is selected from the group consisting of alkylimino-diprorionates, alkylamphoglycinates (mono or di), alkylamphoproprionates (mono or di), alkylaniphoacetates (mono or di), N-alkyl β-aminoproprionic acids, alkylpolyamino carboxylates, phosphorylated imidazolines, and mixtures thereof.

15. The composition of claim 11 wherein the betaine surfactant is selected from the group consisting of alkyl betaines, alkylamido betaines, alkyl sultaines, alkylamido sultaines, and mixtures thereof.

16. The composition of claim 11 wherein the cationic surfactant is selected from the group consisting of mono alkyl quaternaries, di alkyl quaternaries, tri alkyl quaternaries, benzyl quatemaries, ester quatemaries, ethoxylated quatemaries, alkyl amines, and mixtures thereof.

17. The composition of claim 11 wherein the surfactant is selected from the group consisting of cocoamidopropyl betaine, disodium lauroamphodiacetate, sodium laureth sulfate, decyl glucoside, cocoglucoside, POE 80 sorbitan monolaurate, and mixtures thereof.

18. The composition of claim 1 wherein each monoester possesses an HLB of less than or equal to about 11.

19. The composition of claim 18 wherein each monoester possesses an HLB of greater than or equal to about 4 and less than or equal to about 11.

20. A personal care product comprised of the composition of claim 1.

21. The product of claim 20 in the form of a lotion, cream, gel, soap, bath, mousse, tonic, or wash.

22. A kit comprised of:
a) the composition of claim 1; and
b) a cleansing implement.

23. The kit of claim 22 wherein the cleansing implement is a pouf.

24. A makeup remover comprised of the composition of claim 1.

25. A moisturizing detergent composition comprising, based upon the total weight of the composition,
a. from about 0.01 percent to about 5 percent of guar hydroxypropyltrimonium chloride and/or polyquatemium 10;
b. from about 0.1 percent to about 5 percent of di-PPG-2 myreth-10 adipate;
c. from about about 0.1 percent to about 5 percent of a glyceryl ester; and
d. from about 8 percent to about 50 percent a cleansing surfactant.

26. The composition of claim 25 wherein the glyceryl ester is selected from the group consisting of glyceryl oleate, PEG-7 glyceryl cocoate, and mixtures thereof.

27. A personal care product comprised of the composition of claim 25.

28. The product of claim 27 in the form of a lotion, cream, gel, soap, bath, mousse, tonic, or wash.

29. A kit comprised of:
a) the composition of claim 25; and
b) a cleansing implement.

30. The kit of claim 29 wherein the cleansing implement is a pouf.

31. A makeup remover comprised of the composition of claim 25.

* * * * *